July 12, 1960 E. S. BOERNER Plant Pat. 1,958
ROSE PLANT
Filed Oct. 1, 1959
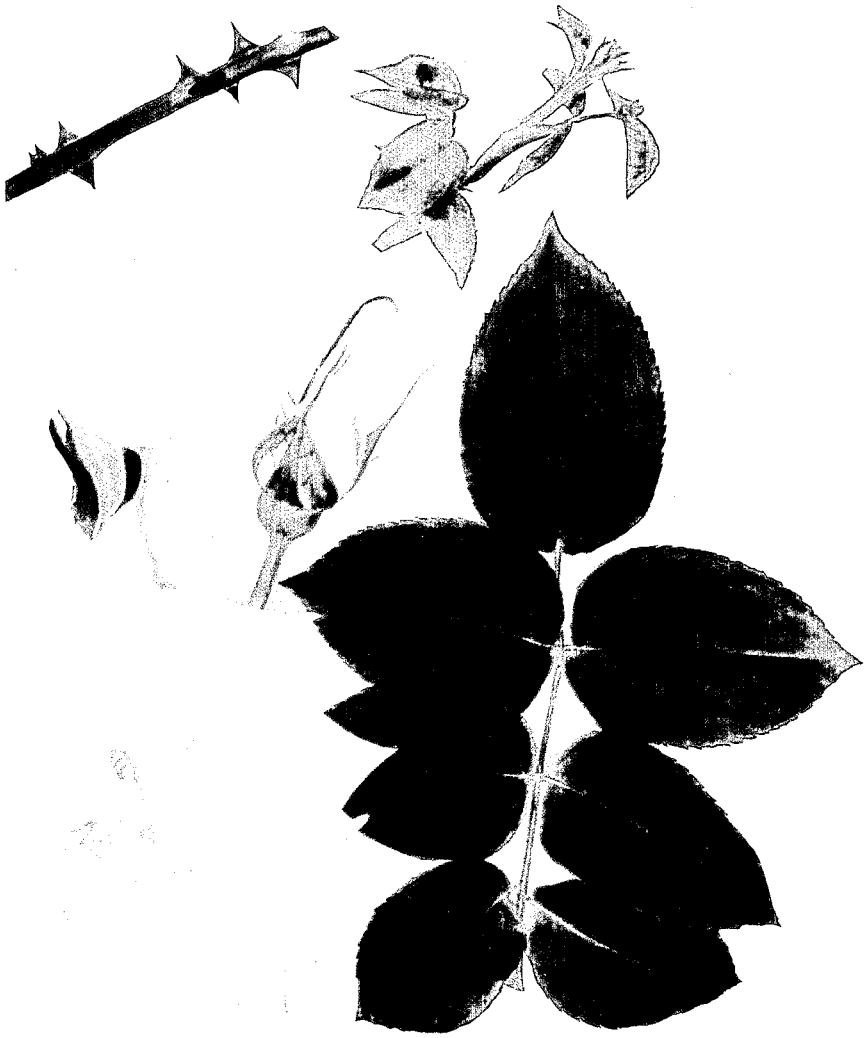
Inventor.
E. S. Boerner
By: Robb & Robb
Attorneys United States Patent Office Plant Pat. 1,958
Patented July 12, 1960

1,958

ROSE PLANT

Eugene S. Boerner, Newark, N.Y., assignor to Jackson & Perkins Company, Newark, N.Y., a corporation of New York Filed Oct. 1, 1959, Ser. No. 843,902

1 Claim. (Cl. 47—61)

The present invention relates to a new and distinct variety of rose plant of the hybrid tea class, which was originated by me by crossing an unnamed and unpatented white seedling derived from a cross of the hybrid tea varieties "Starlite" (Plant Patent No. 414)×"Snow White" (Plant Patent No. 348) with the variety "Golden Masterpiece" (Plant Patent No. 1,284).

The primary objective of this breeding was to obtain an improved hybrid tea rose of long-lasting yellow color and having good form in both the bud and open-flower stages, which is suitable for greenhouse forcing purposes. This objective was fully achieved, along with other desirable improvements, as evidenced by the following unique combination of characteristics which are outstanding in the new variety and which distinguish it from its parents, as well as from all other varieties of which I am aware:

(1) Glossy green foliage which presents a good contrast in combination with yellow flowers;

(2) Freedom of flower production and attendant suitability for greenhouse forcing;

(3) Good form of the flowers in both the bud and open flower stages;

(4) A uniform yellow bud color, corresponding to Empire Yellow in general color tonality, lightly overcast with Martius Yellow on the outer edges of the flower petals, and with no off-colored buds appearing throughout the season and therefore being a substantial improvement over varieties like "Golden Rapture" (unpatented), which has approximately 25 percent off-colored buds of lighter-than-normal yellow;

(5) A double form and slowly opening flower habit;

(6) A distinctive general color tonality of the open flowers corresponding to Empire Yellow, with the outer edges of the flower petals lightly overcast with Baryta Yellow when fully opened;

(7) Prolonged retention of the open flower colors; and (8) The long-lasting qualities of the buds and open flowers which is unusual in yellow hybrid tea roses.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed white seedling derived from "Starlite"×"Snow White."

*Pollen parent.*—"Golden Masterpiece."

Classification:

*Botanic.*—"Hybrid tea."

*Commercial.*—"Hybrid tea."

*Flower*

(Observations made from specimens grown in a greenhouse at Newark, New York, in the late morning during the latter part of April.)

Blooming habit: Recurrent—continuous.

Bud:

*Size.*—Large.

*Form.*—Ovoid; is not affected by wet or hot weather.

*Color.*—When sepals first divide—Citron Yellow, Plate 16. When petals begin to unfurl—Empire Yellow, Plate 4. When half-blown: inside of petals—Empire Yellow, Plate 4, lightly overcast with Martius Yellow, Plate 4, on the outer edges of the petals; reverse of petals—Pinard Yellow, Plate 4, lightly overcast with Empire Yellow, Plate 4, in the lower half of the petals.

*Sepals.*—Branched; curl back when petals begin to unfurl. Color: inside—Kildare Green, Plate 31; outside—Bice Green, Plate 17.

*Calyx.*—Color—Bice Green, Plate 17. Shape—apple. Size—broad. Aspect—smooth. Odor when rubbed—none.

*Peduncle.* — Length — long. Aspect — rough. Strength—stiff; heavy. Color—Spinach Green, Plate 5.

*Opening.*—Opens up well; color of the bud is always uniform; not affected by adverse weather conditions.

Bloom:

*Size.*—Large. Average size when fully expanded—4¼ inches.

*Borne.*—Both singly and several together.

*Stems.*—Long; strong.

*Form (when first open).*—Open. Permanence—retains its form to the end.

*Petalage.*—Double (full but open center). Number of petals under normal conditions—from 40 to 45.

*Color.*—Center of flower—Apricot Yellow, Plate 4. Outer petals—Napthalene Yellow, Plate 16, lightly overcast with Pinard Yellow, Plate 4. Base of petals (aiglet)—Pale Lemon Yellow, Plate 4. Inside of petals—Empire Yellow, Plate 4, with outer edges of petals lightly overcast with Baryta Yellow, Plate 4. Reverse of petals—Napthalene Yellow, Plate 16. General tonality from a distance—Empire Yellow, Plate 4.

*Discoloration.*—General tonality at end of first day—Empire Yellow, Plate 4. Second day—Empire Yellow, Plate 4, with outer edges of petals lightly overcast with Baryta Yellow, Plate 4. Third day—Empire Yellow, Plate 4, with outer edges of petals lightly overcast with Baryta Yellow, Plate 4.

Petals:

*Texture.*—Leathery; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; large.

*Persistence.*—Drop off cleanly.

*Fragrance.*—Moderate. Nature—tea (average hybrid tea scent).

*Lasting quality.*—On the plant—very long. As cut flower—very long.

*Genital organs*

Stamens, anthers: Medium size; many; regularly arranged around styles. Color—Maize Yellow, Plate 4.
Stamens, Filaments (threads): Medium length. Color—Pinard Yellow, Plate 4.
Pollen: Color—Maize Yellow, Plate 4.
Styles: Bunched; uneven length; medium length; thin.
Stigmas: Color—Light Buff, Plate 15.
Ovaries: All enclosed in calyx.
Hips: None.
Seeds: None.

*Plant*

Form: Bush.

Growth: Vigorous; upright.

Foliage: Compound of 3 to 7 leaflets.

*Size.*—Very large.

*Quantity.*—Abundant.

*Color.*—New foliage: upper side—Oil Green, Plate 5, with serrations Oxblood-Red, Plate 1; under side—yellowish Oil-Green, Plate 5, lightly overcast with Van Dyke Red, Plate 13. Old foliage: upper side—Varley's Green, Plate 18; under side—Light Cress Green, Plate 31.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; large.

*Leaf stem.*—Color—Kildare Green, Plate 31. Under side—prickly.

*Stipules.*—Long; bearded.

Wood:

*New wood.*—Color—Spinach Green, Plate 5. Bark—smooth.

*Old wood.*—Color—Forest Green, Plate 17. Bark—smooth.

Thorns:

*Thorns.*—Quantity: on main stalks from base—ordinary; on laterals from stalk—ordinary. Form—flat base; medium length; straight. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of glossy green foliage, with attendant good contrast in combination with yellow flowers, freedom of flower production, with attendant suitability for greenhouse forcing, good form of the flowers in both bud and open stages, a uniform Empire Yellow general color tonality of the buds, lightly overcast with Martius Yellow on the outer edges of the petals, and absence of off-colored buds throughout the season, double form and slow-opening flower habit, a distinctive Empire Yellow general color tonality of the fully open flowers, with the outer edges of the flower petals lightly overcast with Baryta Yellow, prolonged retention of the flower colors, and unusual long-lasting qualities of the buds and open flowers.

No references cited.